United States Patent [19]

Chen et al.

[11] Patent Number: 6,005,139
[45] Date of Patent: Dec. 21, 1999

[54] PROCESS FOR MAKING ALKOXY ESTERS

[75] Inventors: Hang-Chang Bobby Chen, Getzville; Dean R. Lagerwall; Lewis A. Bernstein, both of Amherst, all of N.Y.

[73] Assignee: Occidental Chemical Corporation, Dallas, Tex.

[21] Appl. No.: 09/129,908

[22] Filed: Aug. 6, 1998

[51] Int. Cl.$^6$ .................................................. C07C 69/66
[52] U.S. Cl. ............................................................ 560/187
[58] Field of Search .............................................. 560/187

[56] References Cited

U.S. PATENT DOCUMENTS 2,452,350  10/1948  Bitler et al. ............................. 560/226

OTHER PUBLICATIONS

An Abstract from Bielstein to an article by Michailow et al., in Zpkhab, Ch. Prikl. Khim. vol. 25 (1952) p. 1329.
A Reference from Bielstein to an Article by Scheibler et al., in Jlacbf, Justus Liebigs Ann. Chem. vol. 458 (1927) p. 36.

*Primary Examiner*—Rosalynd Keys
*Attorney, Agent, or Firm*—Anne E. Brookes; Richard D. Fuerle

[57] ABSTRACT

Disclosed is an improved process for reacting a halogenated ester with an alkali metal alkoxide to form an alkoxy ester and a salt. A solvent is added to the halogenated ester prior to the addition of the alkali metal alkoxide. This results in a substantial increase in the particle size of the salt which greatly facilitates its separation from the solution of the alkoxy ester product.

20 Claims, 2 Drawing Sheets

1 μm

PROCESS FOR MAKING ALKOXY ESTERS

BACKGROUND OF THE INVENTION

This invention relates to a process for making an alkoxy ester by reacting a halogenated ester with an alkali metal alkoxide. In particular, it relates to a modification of that process in which solvent is added to the halogenated ester prior to the addition of the alkali metal alkoxide in order to increase the particle size of the salt byproduct that is formed in the reaction.

Ethyl ethoxy acetate (EEA) is used to make a herbicide. At the present time, it is made by reacting ethyl monochloro acetate (EMCA) with a solution of sodium ethoxide in ethanol. Unfortunately, the particle size of the sodium chloride byproduct that is formed is so small that it passes through all but the finest filters and requires days to settle. Even when a medical centrifuge is used to remove the salt from the reaction crude some EEA product and ethanol solvent are lost because they are infused within the finely divided salt bed.

SUMMARY OF THE INVENTION

We have discovered that the reaction of halogenated esters with alkali metal alkoxides can be altered in a simple way which substantially and significantly increases the particle size of the salt byproduct that is formed and slightly improves the yield of the product. We found that when a minimum amount of the solvent was added to the halogenated ester before the addition of the alkali metal alkoxide solution, the average particle size of the salt increased from 0.3 to 0.4 microns up to 9 to 10 microns. As a result, the salt can now be removed from the solvent by conventional industrial solid-liquid separation techniques and little product and solvent are lost with the salt.

DESCRIPTION OF THE PREFERRED EMBODIMENTS

Figure 1:
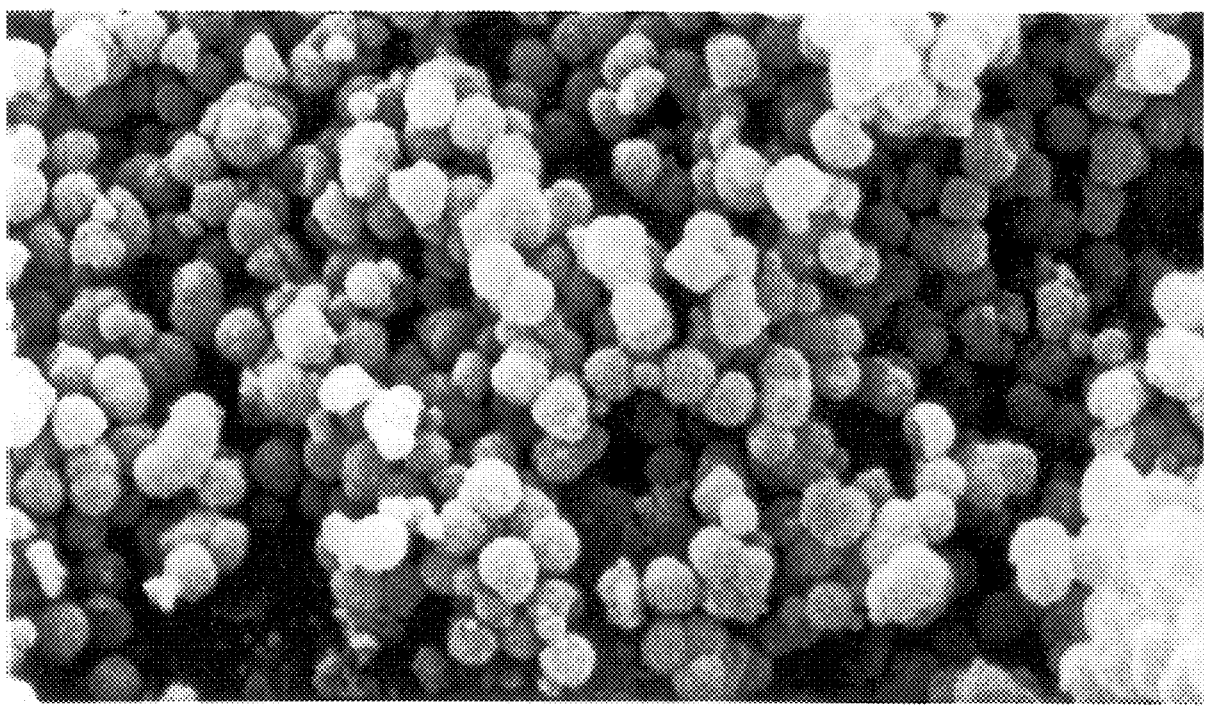
FIG. 1 is a photomicrograph showing particles of sodium chloride that were formed under the prior process for making EEA.

Substrates that can be used in the process of this invention have the general formula

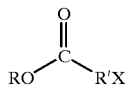

where X is halogen, R is aliphatic from $C_1$ to $C_{18}$ or aromatic from $C_6$ to $C_{18}$, and R' is aliphatic from $C_1$ to $C_{12}$. The X group is preferably chlorine as those substrates are less expensive and more readily available. The R group is preferably alkyl from $C_1$ to $C_8$ and the R' group is preferably alkyl from $C_1$ to $C_8$ as those substrates are more readily available. Examples of substrates that can be used in the process of this invention include EMCA, ethyl monobromo acetate, phenyl monochloro acetate, propyl monochloro acetate, methyl monochloro acetate, and hexyl monochloroacetate. The preferred substrate is EMCA as it is used to make EEA, a commercially important product. The substrate can be a liquid or a solid. Substrates that are soluble in a solvent are preferred because heterogeneous reactions are typically slower.

Alkoxides (alkylates) that can be used in the process of this invention having the general formula MOR", where M is an alkali metal and R" is alkyl or aryl from $C_1$ to $C_{12}$. The M group is preferably sodium as those compounds are less expensive and more readily available and the R" group is preferably alkyl from $C_1$ to $C_6$ for the same reason. Most preferably, the R" group on the alkoxide is identical to the ester group on the substrate (i.e., R"=R) as some ester interchange reactions may occur and this will prevent the formation of unwanted byproducts. The alkali metal alkoxides are solids and can be used in the solid form, but it is preferable to form a solution in a solvent of the alkoxide as that promotes a more rapid reaction. Also, because alkoxides are alkaline and the alkoxy ester product can be unstable if excess alkalinity is present, a solution stabilizes the alkoxy ester. Concentrated solutions are preferred so that less solvent must be processed. Examples of suitable alkoxides include sodium ethoxide, potassium ethoxide, sodium methoxide, potassium methoxide, sodium isopropoxide, sodium phenoxide, sodium butoxide, potassium butoxide, and sodium hexoxide.

The solvents that can be used in the process of this invention should either be inert, and not react with the reactants or the product or, if they do react, they should not react to produce unwanted products. Thus, the organic group in the solvent is preferably the same as the organic group in the alkoxide (i.e., R") and the organic group in the substrate (i.e., R), so that any exchange reactions that occur do not form products other than the desired alkoxy ester. The solvent should be selected so that the byproduct salt has an increased solubility in the reaction mixture relative to the halogenated ester. An increase in the particle size of the salt is not observed with solvents in which the salt is less soluble than the halogenated ester. Generally, the salt will be more soluble in polar organic solvents such as alcohols or glycols, and, for that reason, they are the preferred solvents. However, any solvent that increases the solubility of NaCl in the system can be used. Examples of alcohols and glycols that may be useful include methanol, ethanol, propanol, isopropanol, 1-butanol, 2-methyl-1-propanol, ethylene glycol, and diethylene glycol. Alcohols are also preferred to because they are typically the solvent used with the metal alkoxide solution and the salt byproduct has a reasonable solubility in them.

The process of this invention is preferably performed at room temperature, but heating or cooling can be used if desired. As the reaction is exothermic, some heating will occur in the absence of cooling. While a stoichiometric amount of the alkoxide will react with the substrate (1:1 molar ratio), it is preferable to use a slight excess of alkoxide (0.1 to 5 mole % in excess of stoichiometric) to ensure a complete reaction of the substrate as it may be difficult to separate any unreacted substrate from the product by distillation.

In the process of this invention, some solvent is added to the substrate prior to the addition of the alkoxide. If the alkoxide is in solution it is, of course, preferable to use the same solvent used to form the solution of the alkoxide. A significant increase in the crystal size can require a minimum of 0.01 moles of solvent per mole of substrate, depending on the solvent chosen. However, more than 20 times this minimum amount may provide no significant additional increase in the particle size of the byproduct salt that is formed. For most solvents, about 1/50 to about 2 moles of solvent are used per mole of substrate as that produces the maximum effect on particle size using as little solvent as possible. If the solvent is ethanol, and ethyl ethoxy acetate is being made, about 0.5 to about 100 wt % ethanol is preferably used, based on the weight of EMCA. After the alkoxide has been added to the mixture of the solvent and the substrate, the salt byproduct will gradually precipitate and the product will remain in solution. The solid particles of salt can then be removed by conventional techniques, such as filtration, decantation, or centrifugation. The alkoxy ester product can be separated from the solvent by distillation and the solvent can be recycled.

The following examples further illustrate this invention.

EXAMPLE 1

A 21 wt % solution of sodium ethoxide in ethanol was added to pure EMCA. A solid sodium chloride phase formed immediately. There was little, if any, solubility of the salt in the EMCA. An attempt was made to remove the salt from the solution using a medical centrifuge. However, the salt was so fine that 15 wt % of the EEA and 15 wt % of the ethanol were still lost. FIG. 1 is a photomicrograph at 10 kv and 10,000 magnification showing the resulting particles of sodium chloride.

Figure 2:
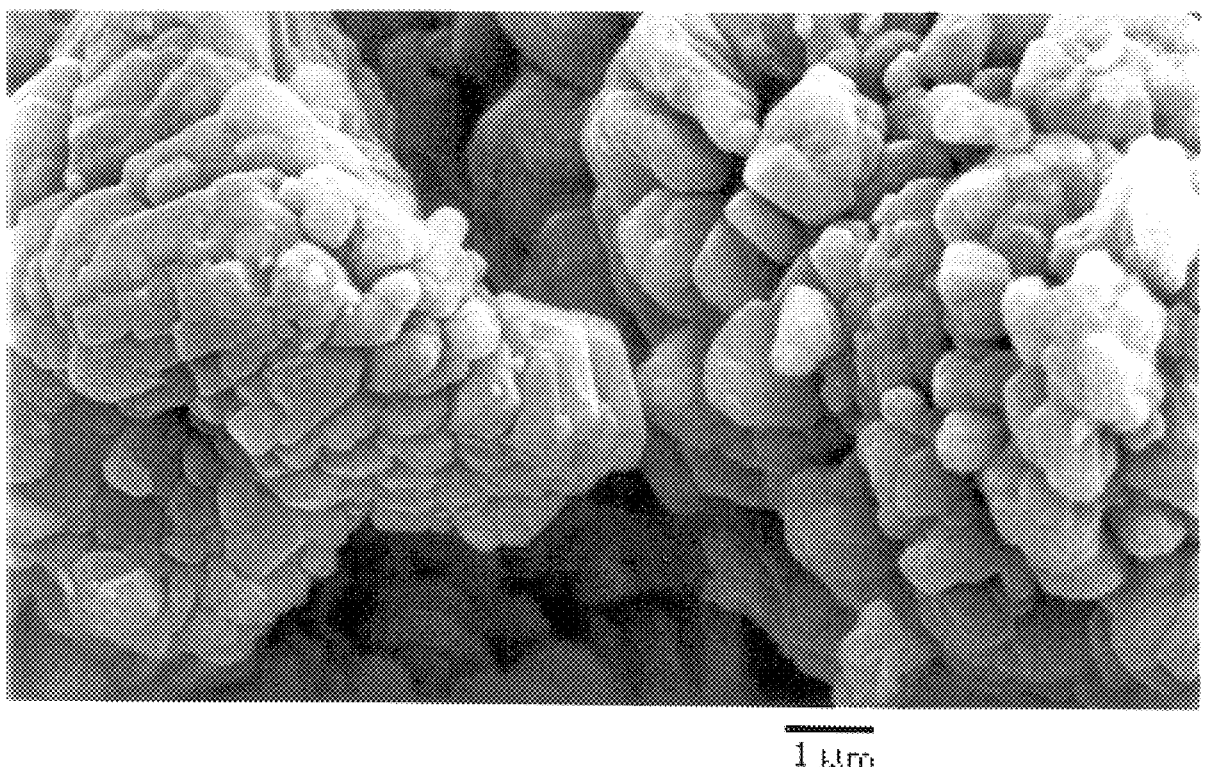
FIG. 2 is a photomicrograph of sodium chloride crystals that were formed using the process of this invention for making EEA.

The above experiment was repeated except that, prior to the addition of sodium ethoxide, ethanol was added to the EMCA at a weight ratio of 2 EMCA:1 ethanol. FIG. 2 is a photomicrograph at 10 kv and 10,000 magnification showing the resulting particles of sodium chloride. FIGS. 1 and 2 show that a remarkable increase in the particle size of the sodium chloride particles occurred when the ethanol was added to the EMCA prior to the addition of the sodium ethoxide.

The following table gives the results of these and similar experiments at other EMCA to ethanol (EtOH) weight ratios.

| Weight ratio (EMCA:EtOH) | no EtOH | 8:1 | 4:1 | 2:1 | 1:1 | 1:1.5 |
|---|---|---|---|---|---|---|
| Resulting % EEA | 30.1 | 29.1 | 28.1 | 26.3 | 23.4 | 21.0 |
| Resulting % EtOH | 56.6 | 58.1 | 59.6 | 62.1 | 66.4 | 69.7 |
| Resulting % NaCl | 13.3 | 12.8 | 12.4 | 11.6 | 10.3 | 9.2 |
| Particle Diameter (microns)** | | Percent of Each Particle Size | | | | |
| 0.2–0.3 | 10.5 | | | | | |
| 0.3–0.4 | 59.8 | | | | | |
| 0.4–0.5 | 22.7 | | | | | |
| 0.5–1.0 | 7 | | | | | |
| 1–2 | | | | | | |
| 2–3 | | 33.7 | 4.8 | | | |
| 3–4 | | 66.3 | 50.9 | | 25.2 | |
| 5–6 | | | 33.9 | 7.8 | 46 | 7.3 |
| 7–8 | | | 10.4 | 26.3 | 23 | 26.8 |
| 9–10 | | | | 31.5 | 5.8 | 37.6 |
| 11–12 | | | | 21.2 | | 17.8 |
| 13–14 | | | | 10.2 | | 7.9 |
| 15–16 | | | | 3 | | 2.6 |
| 95% of salt settled by: | 4100 min | | | 40 min | | |
| 99% complete salt settling by: | 7000 min | | | 60 min | | |
| % salt bed depth (vol) | 29% | | | 12% | | |

The table shows that the particle size of the salt was significantly larger when ethanol was added and that the salt settled much faster and more compactly.

EXAMPLE 2

Four vials were charged with EMCA. An alcoholic solvent was charged to three of the vials at a 2:1 weight ratio of EMCA to alcohol. To all four vials was added 21 wt % sodium ethylate in ethanol. The settling of the salt in the vials was compared. The following table gives the results:

| | Salt Cake Depth (% from top of liquid) | |
|---|---|---|
| | After 1 hour | Final |
| No solvent | 43 | 29 (>64 hrs) |
| Methanol | 12 | 12 |
| Ethanol | 12 | 12 |
| Diethylene glycol | 25 | 25 |

The table shows that the addition of the alcohol caused the salt to settle more rapidly and more compactly.

We claim:

1. A method of reacting a halogenated ester with an alkali metal alkoxide to form an alkoxy ester and a salt comprising (A) forming a mixture of said halogenated ester and at least about 0.01 moles of a solvent per mole of said halogenated ester, where said salt has an increased solubility in said solvent relative to said halogenated ester;

(B) adding to said mixture about a stoichiometric amount of an alkali metal alkoxide, whereby said halogenated ester and said alkali metal alkoxide react to form said alkoxy ester and said salt, wherein said salt precipitates with an enhanced particle size; and (C) separating said precipitated salt from said solvent.

2. A method according to claim 1 wherein said halogenated ester has the general formula:

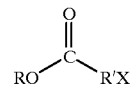

where X is halogen, R is aliphatic from $C_1$ to $C_{18}$ or aromatic from $C_6$ to $C_{18}$ and R' is aliphatic from $C_1$ to $C_{12}$.

3. A method according to claim 2 wherein X is chlorine.

4. A method according to claim 2 wherein R is alkyl from $C_1$ to $C_8$.

5. A method according to claim 2 wherein R' is alkyl from $C_1$ to $C_8$.

6. A method according to claim 1 wherein said halogenated ester and said alkali metal alkoxide are soluble in said solvent.

7. A method according to claim 1 wherein said alkali metal alkoxide is added in a solution of said solvent.

8. A method according to claim 2 wherein said solvent is ROH.

9. A method according to claim 2 wherein said alkoxide is NaOR.

10. A method according to claim 1 wherein said halogenated ester is monochloro ethyl acetate, said alkali metal alkoxide is sodium ethoxide, and said solvent is ethanol.

11. A method according to claim 1 wherein said solvent is methanol, ethanol, propanol, isopropanol, 1-butanol, 2-methyl-1-propanol, ethylene glycol, or diethylene glycol.

12. A method of reacting a chlorinated ester with an alkali metal alkoxide to form an alkoxy ester and a salt comprising (A) forming a solution of a halogenated ester having the general formula

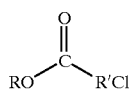

in about 0.02 to about 2 moles, per mole of said chlorinated ester, of an alcohol having the formula ROH;

(B) reacting to said chlorinated ester with an alkali metal alkoxide having the general formula MOR" in a solution of said alcohol to form a solution of said alkoxy ester and a precipitate of said salt having an enhanced particle size; and (C) separating said precipitate from said alkoxy ester, where R is alkyl from $C_1$ to $C_8$, R' is alkyl from $C_1$ to $C_8$, and R" is alkyl from $C_1$ to $C_6$.

13. A method according to claim 12 wherein R, R', and R" are ethyl.

14. A method according to claim 12 wherein the amount of said alkali metal alkoxide is about 0.01 to about 0.1 mole % in excess of stoichiometric.

15. A method of making ethyl ethoxy acetate and a sodium chloride byproduct having an enhanced particle size comprising (A) forming a mixture of ethyl monochloro acetate and about 0.5 to about 100 wt % of ethanol, based on the weight of said ethyl monochloro acetate;

(B) adding to said mixture a solution in ethanol of about a stoichiometric amount of sodium ethoxide, whereby said ethyl monochloro acetate and said sodium ethoxide react to form a solution of ethyl ethoxy acetate and precipitated sodium chloride having an enhanced particle size; and (C) separating said precipitated sodium chloride from said solution.

16. A method according to claim 15 wherein the amount of said sodium ethoxide is about 0.1 to about 5 mole % in excess of stoichiometric.

17. A method according to claim 15 including the additional last step of isolating said ethyl ethoxy acetate by distilling said solution of ethyl ethoxy acetate in ethanol.

18. A method according to claim 17 wherein said ethanol that is distilled is recycled.

19. A method according to claim 15 wherein said ethyl monochloro acetate, said sodium ethoxide, and said ethanol are at room temperature when they are mixed.

20. A method according to claim 15 wherein said precipitated sodium chloride is removed by filtration.

* * * * *